US007691900B2

United States Patent
Luu et al.

(10) Patent No.: US 7,691,900 B2
(45) Date of Patent: Apr. 6, 2010

(54) TOCOPHEROL DERIVATIVES WITH A LONG HYDROXYLATED CHAIN, WHICH CAN BE USED AS NEUROTROPHICS

(75) Inventors: Bang Luu, Strasbourg (FR); Paul Heuschling, Garnich (LU); Thierry Muller, Ettelbruck (LU); Eleonora Morga, Luxembourg (LU)

(73) Assignee: AxoGlia Therapeutics S.A., Luxembourg (LU)

( * ) Notice: Subject to any disclaimer, the term of this patent is extended or adjusted under 35 U.S.C. 154(b) by 1050 days.

(21) Appl. No.: 10/572,933

(22) PCT Filed: Sep. 24, 2004

(86) PCT No.: PCT/FR2004/002424

§ 371 (c)(1),
(2), (4) Date: Mar. 22, 2006

(87) PCT Pub. No.: WO2005/030748

PCT Pub. Date: Apr. 7, 2005

(65) Prior Publication Data

US 2007/0105946 A1 May 10, 2007

(30) Foreign Application Priority Data

Sep. 26, 2003 (FR) .................. 03 11325

(51) Int. Cl.
*A01N 43/02* (2006.01)
*A01N 43/16* (2006.01)
*A61K 31/335* (2006.01)
*A61K 31/35* (2006.01)

(52) U.S. Cl. ............ 514/458; 514/449; 514/450; 514/451; 514/453; 514/456

(58) Field of Classification Search ........ 514/449, 514/450, 451, 453, 456, 458
See application file for complete search history.

(56) References Cited

U.S. PATENT DOCUMENTS

2002/0006954 A1 * 1/2002 Hensley et al. ............. 514/458

FOREIGN PATENT DOCUMENTS

WO 94/11343 5/1994
WO 03/068741 A1 8/2003

* cited by examiner

*Primary Examiner*—Yong S Chong
(74) *Attorney, Agent, or Firm*—The Nath Law Group

(57) ABSTRACT

The invention relates to any isolated or synthetic compound and, in particular, to compounds having formula which can: modulate the cell specification of neural stem cells, promote the differentiation and subsequent survival of differentiating glial cells and neurones, and promote the differentiation of oligodendrocyte precursor cells into mature oligodendrocytes. In addition, the inventive compounds can reduce the inflammatory component of diseases that affect the nervous system, for example, by reducing activation of the microglia an/or astrocytes and/or by reducing reactive gliosis. The invention also relates to the methods of preparing such compounds and to the use of same in the preparation of a pharmaceutical composition that is intended for the prevention or treatment of diseases that affect the nervous system. More specifically, the inventive compounds have general formula.

11 Claims, No Drawings

TOCOPHEROL DERIVATIVES WITH A LONG HYDROXYLATED CHAIN, WHICH CAN BE USED AS NEUROTROPHICS

The present invention relates to any isolated or synthetic compound and in particular to the compounds of Formula (I), which can modulate the cellular specification of the neural stem cells (modulation of the ratio neuron/glial cells), promote the differentiation and the subsequent survival of the neurons and glial cells during differentiation as well as the differentiation of oligodendrocyte precursor cells into mature oligodendrocytes. In addition, the compounds according to the invention are able to reduce the inflammatory component of diseases that affect the nervous system, notably by reducing the activation of the microglia and/or the astrocytes and/or by reducing reactive gliosis. The invention also relates to compositions comprising these compounds as well as methods for the preparation of such compounds and their use in the preparation of a pharmaceutical composition intended for the prevention or treatment of diseases that affect the nervous system.

The central nervous system (CNS) is constituted by two cellular populations that can be characterised as neural cells: the neurons, and all other types of cells, classified under the name of glial cells. The astrocytes and the oligodendrocytes represent the principal types of glial cells in the adult. These cells are produced throughout the foetal life and their production continues after birth and up to adulthood in certain regions of the brain.

Neurons, astrocytes and oligodendrocytes are derived from a common precursor, a multipotential cell possessing theoretically unlimited proliferation abilities and which is located in the neural tube. These precursors can be considered as neural stem cells as they fulfil the criteria that define stem cells: self-renewal, almost infinite ability to proliferate and ability to generate the types of cells that make up the tissue from which they-originate.

The neuron, a hyper specialised cell, develops in a support tissue and in the environment of the glia. The central glia is composed of glial cells from the central nervous system, and the peripheral glia is composed of glial cells from the peripheral nervous system. More exactly, the central glia comprises astrocytes (astroglia), oligodendrocytes (oligodendroglia) and microgliocytes (microglia). The peripheral glia comprises Schwann cells, equivalent to the oligodendrocytes of the central glia.

The astrocytes are constituents of the hematoencephalic barrier (BHE). They are involved in the regulation of the cerebral metabolism and act as the interface between the capillaries and the neurons (nutritive role) by means of projections (pseudopods) that wrap around the capillaries. They participate in the recapture of the neurotransmitters and are also involved in healing by producing glial filaments (constituents of the cytoskeleton).

The microgliocytes are glial cells that originate from the myeloid family invading the central nervous system during the embryonic period. The microglia is specialised in the elimination of macromolecules, phagocytosis of cells in apoptosis or in necrosis, the recognition and elimination of pathogens, as well as in the regulation of the immunity response.

The oligodendrocytes provide myelination of the axons in the central nervous system. The oligodendrocytes originate from a variety of progenitors. These cells are generated in very limited ventricular zones all along the neural tube. In the adult, the oligodendrocytes are dispersed throughout the cerebral parenchyma, with a predominance in the clusters of white matter.

The myelin sheath, synthesised by the oligodendrocyte, is a membrane-associated protein that wraps around the axons. It possesses a dual function: it acts as an electrical insulation and especially permits the speed of propagation of the nerve impulse to be increased. A disruption to this sheath leads to a slowing down, even halting the possibility of movement, perturbing the nervous transmission of information and provoking neurological disorders. The loss or the poor state of the myelin brings about the occurrence of 'demyelinising' or 'dysmyelinising' diseases. The commonest and the most devastating of these diseases is multiple sclerosis (MS).

Multiple sclerosis is a neurological disease of the young adult which associates a demyelination with inflammatory or even immunological elements. Present-day treatments deal relatively well with the inflammatory component. However, they have no effect on the demyelination aspect, which causes a permanent and cumulative handicap. Unlike what was thought previously, it has been proved that even in the early stages of the disease, the oligodendrocytes retain the possibility of fabricating new myelin (remyelination). On the other hand, in the chronic phase, this capability of remyelination seems to be completely lost. For the majority of patients, MS is known to evolve initially by "relapsing and remitting", and then in a "progressive" form. It appears that the oligodendrocytes and their precursors can survive the inflammatory phenomena of the initial phase, however their number and their efficiency are considerably reduced during the chronic phase. Two therapeutic possibilities have been considered so far: transplantation of precursors of oligodendrocytes (graft) or a stimulation of the myelination by chemical substances on the surviving oligodendrocytes and precursors of endogenous oligodendrocytes (endogenous remyelination).

For the transplantation, the use of precursors of oligodendrocytes (scarcely differentiated young cells) suggested as having greater possibilities of synthesising myelin and migration than the adult oligodendrocytes, has been considered in the prior art for repairing a maximum volume of demyelinised zones. The ideal source of oligodendrocytes would be very young human nervous tissue (embryonic); this raises ethical and practical considerations. Moreover, their migratory properties are unknown. For the majority of patients, there are a great number of lesions and it is inconceivable to graft each one individually. Furthermore, it is still unknown if these oligodendrocytes are capable of migrating by themselves or whether the intervention of specific chemical factors is necessary, and the lifetime of the cells is also unknown.

In addition, different peptidic substances, identified above as neurotrophic factors, have been described in the prior art (Recent progress in the studies of neurotrophic factors and their clinical implications, L. Shen, A. Figurov & B. Luu, Journal of Molecular Medicine, 1997, vol. 75, 637-644). They are growth factors specific for the brain. They protect the nerve cells against a variety of aggressions, particularly against substances liberated by the activated microglial cells and responsible for the inflammation of the brain as well as against diverse diseases caused by the malfunction of the nervous system. In general, these neurotrophic factors increase the survival of the nerve cells, favour their differentiation, i.e. their full development, and render them usable.

In the context of the present invention, the inventors have looked into the possible effects of novel compounds on the stem cells (Stem cells—Clinical application and Perspectives, M. Brehm, T. Zeus & B. E. Strauer, Herz, 2002, vol. 27, 611-620). Indeed, recent discoveries lead us to believe that a significant chapter is beginning to unfold in biomedicine. These stem cells could be indispensable tools for a new branch of medicine known as regenerative medicine. (Stem cells for regenerative medicine: advances in the engineering of tissues and organs, J. Ringe, C. Kaps, G. R. Burmester & M. Sittinger, 2002, vol. 89, 338-351) (Regenerating the damaged central nervous system, P. J. Horner & F. H. Gage, Nature, 2000, vol. 407, 963-970). This medicine would find powerful applications for treating age-related diseases, degenerative neuropathies (Human stem cells as targets for the aging and diseases of aging processes, Medical Hypotheses, 2003, vol. 60, N 3, 439447) and for post traumatic complaints of the nervous system.

The mechanisms by which a neural stem cell creates three major types of cells of the CNS are still little known. However, it is known that this development proceeds by successive steps, during which the developmental potentialities of the neural stem cell are progressively restricted. Thus, intermediate precursors with more and more limited potentialities are produced, which lead to highly differentiated cells. Initially, the stem cells are of embryonic origin. Thus, they are present essentially in the foetus and young children. They can multiply almost infinitely. The neurotrophic factors cause them to transform into mature and different types of functional cells (Neurons and astrocytes secrete factors that cause stem cells to differentiate into neurons and astrocytes, respectively, M. Y. Chang, H. Son, Y. S. Lee & S. H. Lee, Molecular and Cellular Neuroscience 2003, vol. 23 N 3, 414-426). Very recently, it has been shown that stem cells are also present in more developed organs, particularly in the brain (Adult Neurogenesis and Neural Stem Cells of the Central Nervous System in Mammals, Ph. Taupin & F. H. Gage, Journal of Neuroscience Research, 2002, vol. 69, 745-749) and the adult spinal chord. Therefore, under the action of different growth factors, neural stem cells, i.e. the stem cells present in the brain, can transform into neurons, astrocytes or oligodendrocytes, i.e. the principal types of nerve cells.

However, due to their molecular size and their physicochemical properties, the proteic growth factors are unable to cross various biological barriers, particularly the hematoencephalic barrier. They are therefore unable to penetrate into the brain in sufficient quantity to produce any beneficial effect. Moreover, they have a very poor bioavailability and thus their efficiency and use are limited.

The invention now proposes an advantageous alternative to transplantation, consisting in the use of novel compounds. These novel compounds are able to cross the hematoencephalic barrier and favour an endogenous remyelination by modulating the cellular specification of the neural stem cells (modulation of the ratio neuron/glial cells) and/or favouring the differentiation of the precursors of oligodendrocytes into oligodendrocytes. In fact, the present invention describes the development of small hydrophobic molecules capable of firstly penetrating into the brain in sufficient quantity to promote a desired biological effect and secondly, to mimic the action of certain neurotrophic factors. These mimics are able to transform in situ, in the brain, the neural stem cells into differentiated nerve cells as well as the precursors of oligodendrocytes into oligodendrocytes. Thus, this alternative obviates any surgical intervention.

Indeed, when the stem cells are used for the treatment of degenerative neuropathies, they are introduced into the brain by means of a surgical operation (Neural stem cells in the developing central nervous system: implications for cell therapy through transplantation, C. N. Svendsen & M. A. Caldwell, Progress in Brain Research, 2000, vol. 127, 13-34), just as the oligodendrocyte precursors can be. Accordingly, the inventors have developed and synthesised compounds capable of modulating, in vivo, ex vivo or in vitro the cellular specification of the neural stem cells, i.e. to influence the choice for a neural stem cell to tend towards the neuronal path or the glial path (modulation of the ratio neuron/glial cells). Moreover, these compounds are capable of promoting the differentiation and then the survival of the neurons and glial cells in differentiation. More specifically, the compounds according to the invention favour the neuronal survival and the growth of the neurites. The compounds according to the invention are equally capable of favouring the differentiation of precursor oligodendrocyte cells into mature oligodendrocytes. The compounds according to the invention are also able to reduce the inflammatory component in diseases that affect the nervous system. Specifically, they can also reduce the activation of the microglia and/or the astrocytes. Moreover, these compounds are capable of reducing the reactive gliosis, i.e. the glial scarring, more specifically by modulating the expression of certain compounds of the cytoskeleton of the astrocytes.

Accordingly, a first subject of the invention relates to any isolated or synthetic compound that in vivo, in vitro or ex vivo, provokes the modulation of the specification of neural stem cells and/or the differentiation of oligodendrocyte precursor cells into oligodendroglial cells and/or represses the activation of the microglial cells and/or the activation of the astrocytes and/or the reactive gliosis.

Preferably, the invention relates to any isolated or synthetic compound that in vivo, in vitro or ex vivo, provokes the modulation of the specification of neural stem cells and/or the differentiation of oligodendrocyte precursor cells into oligodendroglial cells and/or represses the activation of the microglial cells and/or the activation of the astrocytes and/or the reactive gliosis. It also relates to the use of such a compound in vivo to modulate, preferably to repress the activation of the microglial cells, in the manner of non-steroidal anti-inflammatory compounds (NSAIDs), the latter being incapable, however, contrary to the compounds or compositions according to the invention, of crossing the hematoencephalic barrier.

The compounds according to the invention are excellent agents for the treatment of neurodegenerative or demyelinising/dysmyelinising diseases, such as notably multiple sclerosis, Alzheimer's disease, Parkinson's disease, Creutzfeldt-Jakob disease, but also vascular dementia, amyotrophic lateral sclerosis, infantile spinal amyotrophies and neuropathies linked to cerebral vascular accidents. The invention also relates to their preparation processes and the pharmaceutical compositions comprising them.

A particular subject of the present invention is long chain hydrocarbon alcohols, substituted by a ring of the tocopherol type, as well as their analogs. These compounds are called tocopherol fatty alcohols (TFA).

The compounds according to the invention preferably comprise a long chain ω-alkanol and a ring of the tocopherol type. Such compounds that possess a suitably sized chain length and properly chosen substituents are capable of modulating the cellular specification in the neural stem cells, to favour the differentiation, neuronal survival and neuritic growth as well as the differentiation and the survival of the oligodendroglial cells. As indicated previously, the compounds are also able to reduce the inflammatory component that arises during diseases that affect the nervous system. More specifically, these compounds can reduce or repress the activation of the microglia as well as that of the astrocytes. These compounds can also reduce the reactive gliosis, more specifically by modulating the expression of certain compounds of the cytoskeleton of the astrocytes. The repression of the activation of the microglial cells and the transformation of the neural stem cells into mature oligodendrocytic cells are the essential characteristics for the treatment of neurodegenerative or demyelinising/dysmyelinising type diseases like multiple sclerosis.

A particular subject of the invention accordingly relates to compounds represented by the general Formula (I):

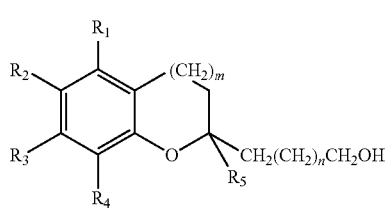

wherein
$R_1$, $R_2$, $R_3$ and $R_4$, identical or different, represent a hydrogen atom, a hydroxyl group, a linear or branched ($C_1$-$C_6$) alkyl group, a linear or branched ($C_1$-$C_6$) alkoxy group, a linear or branched ($C_1$-$C_6$) carboxylate group,
$R_5$ represents a hydrogen atom or a linear or branched ($C_1$-$C_6$) alkyl group,
m is an integer between 0 and 2, preferably between 1 and 2, and
n is an integer between 8 and 25, preferably between 8 and 20, even more preferably between 8 and 16 or between 8 and 14.

Formula (I) is therefore made up of an aromatic ring fused to a 5, 6 or 7-membered ring (m=0, 1, 2), that is, a benzofuran, a benzopyran or one their higher homologs. Preferably, it is a benzopyran. Preferably, m is equal to 1.

The compounds of Formula (I) include compounds in which the carbon atom that bears the substituent $R_5$ has the R,S configuration or is a mixture (preferably racemic).

According to the invention, the term "alkyl" designates a linear or branched hydrocarbon group having advantageously 1 to 6 carbon atoms, such as methyl, ethyl, propyl, isopropyl, butyl, isobutyl, tert-butyl, pentyl, neopentyl, n-hexyl, etc. When at least one $R_1$, $R_2$, $R_3$ and $R_4$ represents an alkyl group, then methyl, ethyl, isopropyl, or tert.-butyl groups are preferred.

The alkoxy groups correspond to the alkyl groups defined above, linked to the remainder of the molecule through a —O— bond (ether). $C_1$-$C_6$ groups are particularly preferred, especially methoxy, ethoxy, isopropoxy, or a tert-butoxy group.

The carboxylate groups correspond to —OCO-alkyl groups, the term alkyl being defined as above, such as acetate, a propionate, a butyrate, a pentanoate or a hexanoate.

According to a particular aspect of the invention, compounds of Formula (I) correspond to those in which at least one, preferably only one, of the substituents $R_1$, $R_2$, $R_3$ and/or $R_4$ on the aromatic ring, represent a hydroxyl, an alkoxy or carboxylate group.

According to another particular aspect of the invention, $R_5$ represents a hydrogen atom or an alkyl group, preferably methyl, with an R,S configuration or is a mixture (preferably racemic).

The side chain of the compound of Formula (I) therefore corresponds to a ω-alkanol in which n is comprised between 8 and 25, preferably between 8 and 20, even more preferably between 8 and 16 or between 8 and 14. Compounds of Formula (I) in which n is equal to 10, 11, 12, 13, 14, 15 or 16 are particularly effective compounds in the context of the present invention. Compounds possessing a side chain with at least 12 carbon atoms and at most 18 carbon atoms i.e. TFA-12, TFA-14, TFA-15, TFA-16 and TFA-18, are particularly preferred. Other compounds that can be synthesised according to a procedure such as that described below, in which $R_1$, $R_2$, $R_3$ and $R_4$ are methoxy groups or acetate groups, their side chain having the same number of carbon atoms as described previously, are equally effective.

Accordingly, a subject of the invention relates to a pharmaceutical composition comprising as the active substance at least one isolated or synthetic compound capable of modulating, in vivo, in vitro or ex vivo, the cellular specification of the neural stem cells, to favourise in vivo, in vitro or ex vivo, the differentiation of the neural stem cells and/or the precursor cells of oligodendrocytes into oligodendroglial cells and the survival of said oligodendroglial cells or on the contrary to favour the differentiation of the neural stem cells into neurons and the survival of said neurons, or further to modulate, preferably to repress, the activation of the microglial cells and/or the activation of the astrocytes and/or the reactive gliosis, in association with a pharmaceutically acceptable carrier. A preferred pharmaceutical composition in the sense of the invention comprises as the active substance at least one isolated or synthetic compound capable of modulating the specification of the neural stem cells and/or to provoke the differentiation of the precursor cells of oligodendrocytes into oligodendroglial cells, and/or the modulation, preferably the repression or the reduction of the activation of microglial cells and/or astrocytes, and/or to modulate, preferably repress the reactive gliosis, in association with a pharmaceutically acceptable carrier.

Another subject of the present invention also relates to pharmaceutical compositions comprising as the active substance at least one compound according to the general Formula (I) of the invention, as described previously, in association with a pharmaceutically acceptable carrier or excipient.

Whatever the chosen route of administration, the preferred compositions according to the invention are in a form that favours the protection and the optimum assimilation of the active principle.

The compounds or compositions according to the invention can be administered in different ways and in different forms. Thus, they can be administered in a systemic manner, orally, by inhalation or by injection, such as, for example, intravenously, intramuscularly, subcutaneously, transdermally, intra-arterially, etc., intravenously, intramuscularly, subcutaneously, orally and by inhalation being preferred.

For injections, the compounds are generally packaged in the form of liquid suspensions that can be injected by means of syringes or by perfusion, for example. In this regard, the compounds are generally dissolved in saline, physiological, isotonic, buffered, etc., solutions that are compatible with a pharmaceutical usage and known to the person skilled in the art. Thus, the compositions can comprise one or a plurality of agents or media selected among dispersants, solubilisers, stabilisers, preservatives, etc. The useable agents or media in the liquid and/or injectable formulations are principally methyl cellulose, hydroxymethyl cellulose, carboxymethyl cellulose, polysorbate 80, mannitol, gelatin, lactose, vegetal oils, acacia, etc.

The compounds can also be administered in the form of gels, oils, tablets, suppositories, powders, gel capsules, capsules, aerosols, etc, possibly by means of galenical forms or by devices that ensure a prolonged and/or delayed release. An agent, such as cellulose, carbonates or starches, is advantageously used for this type of formulation.

In particular, the compounds according to the invention can modulate the activation of the microglial and astrocytic cells in concentrations of $10^{-5}$ to $10^{-12}$, preferably $10^{-6}$ to $10^{-8}$M, even more preferably $10^{-5}$ to $10^{-8}$ M. At the same preferred concentration conditions, these compounds transform the oligodendrocyte precursor cells into mature oligodendrocytes. In these conditions, the compounds according to the invention can also favour the differentiation and the survival of the neurons.

The inventors, having demonstrated an activity of the compounds according to the invention at the above-indicated concentrations, it should be understood that the rate and/or the injected dose can be adapted by the person skilled in the art as a function of the patient, the pathology in question, the route of administration, etc. Moreover, when necessary, repeated injections can be carried out. Furthermore, delayed or prolonged release systems can be advantageous for chronic treatments.

In addition, the invention relates to the use of a compound for the preparation of a pharmaceutical composition intended for the prevention or treatment of diseases that affect the nervous system, which alter the oligodendrocytes or the other cells of the central nervous system, and/or the inflammation of the nervous system. Such diseases principally include the degenerative neuropathies and in particular the demyelinising or dysmyelinising diseases as well as Alzheimer's disease.

In the scope of the invention, the term "treatment" is understood to mean both a preventative and a curative treatment, which can be used alone or in combination with other agents or treatments.

Moreover, it can be a treatment for chronic or acute disorders.

Therefore, the TFA compounds, as described above, can be used as pharmaceutical agents in the treatment of neurodegenerative diseases and demyelinising diseases, in particular for multiple sclerosis.

Another subject of the invention relates to the use of a compound or a composition according to the invention, which induces in vivo the modulation of the cellular specification of the neural stem cells, the differentiation and the survival of the neurons and the oligodendrocytes, the modulation of the microglial and astrocytic activation as well as the reactive gliosis.

Another subject of the invention relates to the use of a compound or a composition according to the invention for the treatment, ex vivo, of stem cells or oligodendrocyte precursor cells, such as described previously. In particular, this treatment consists in inducing the specification and/or the differentiation of said cells.

The invention also relates to a method of treatment for the prevention or curing of diseases of the nervous system which alter the oligodendrocytes or their activity and/or the inflammation of the nervous system, comprising the administration to a patient affected by such a pathology or presenting a risk of developing it, of an effective quantity of a compound or a composition according to the invention, for example a compound obeying Formula (I), or even of stem cells or oligodendrocyte precursor cells treated ex vivo, as indicated above.

The diseases that could be treated with a compound according to the invention are particularly multiple sclerosis, Alzheimer's disease, Parkinson's disease, Creutzfeldt-Jakob disease. Other diseases that could be treated are vascular dementia, amyotrophic lateral sclerosis, infantile spinal amyotrophies. Similarly, lesions that originate from cerebral vascular accidents and all other lesional attacks of the nervous system could be treated by the compounds and compositions of the invention.

The compounds of the invention can be prepared from commercial products, by means of a combination of chemical reactions known to a person skilled in the art, possibly based on the preparation process for the compounds of general Formula (I) as described below.

The compounds of the general Formula (I) can notably be obtained using a preparation process comprising the following steps: formation of a Weinreb amide, an addition-elimination, a Grignard addition and a coupling reaction catalysed by $ZnCl_2$ and HCl.

A compound according to Formula (I) can, for example, be prepared according to the particular reaction scheme below:

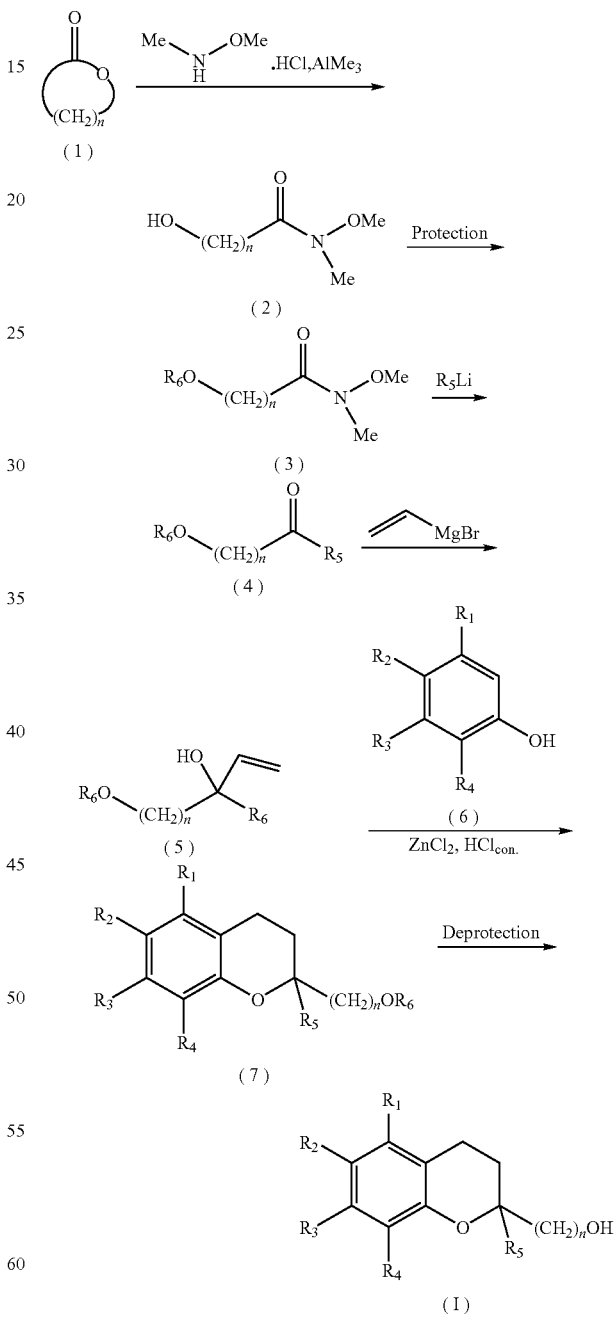

wherein:

$R_1$, $R_2$, $R_3$, $R_4$, $R_5$ and n have the same meaning as described previously.

$R_6$ represents a benzyl group or a tert-butyldimethylsilyl group.

More specifically, compound (I) is prepared by the reaction of compound (1) with dimethylhydroxylamine in the presence of trimethylaluminium to afford compound (2), the alcohol function of which is subsequently protected to afford compound (3). A nucleophilic addition of an organolithium compound on compound (3) affords compound (4), which, in the presence of a vinylmagnesium gives compound (5). The reaction between compound (5) and compound (6) in the presence of zinc and hydrochloric acid affords compound (7) that after deprotection of the alcohol function, affords compound (I).

More specifically, compound (I) where $R_1$, $R_3$, $R_4$, $R_5$ are methyl groups, $R_2$ is a hydroxyl group, m=1 and n=13 can be prepared in the following manner: Oxacycloheptadecan-2-one reacts with dimethylhydroxylamine in the presence of trimethylaluminium at 0° C. and at atmospheric pressure to yield N-methoxy-N-methyl-16-hydroxyhexadecanamide. The hydroxy function of this compound is then protected in the presence of sodium hydride and benzyl bromide at −78° C. and atmospheric pressure. The resulting N-methoxy-N-methyl-16-benzyloxyhexadecanamide is subsequently treated with methyllithium at −78° C. and at atmospheric pressure to yield 17-benzyloxyheptadecan-2-one. This reacts with the vinylmagnesium to afford 18-benzyloxy-3-methyloctadec-1-en-3-ol that in the presence of trimethylhydroquinone, zinc chloride and concentrated hydrochloric acid yields 2-(15-benzyloxypentadecyl)-2,5,7,8-tetramethylchroman-6-ol. Catalytic hydrogenation of this compound in the presence of palladium on charcoal affords 2-(15-hydroxypentadecyl)-2,5,7,8-tetramethylchroman-6-ol.

In addition, the invention relates to tools and kits intended for the procedures involving one or the other of the methods such as described above.

Other aspects and advantages of the present invention will become apparent on reading the illustrative and non-limiting examples that follow.

EXAMPLES

A. Preparation of a Compound of Formula (I)

1. Preparation of N-methoxy-N-methyl-16-hydroxyhexadecanamide 1.78 g of dimethylhydroxylamine (17.687 mmol; 3 eq.; MW=97.55) were dissolved in 10 mL of $CH_2Cl_2$ that had been distilled under argon and cooled to −78° C. 8.8 mL of $AlMe_3$, 2M in hexane, (17.687 mmol; 3 eq.; MW=72.09) were added drop by drop at −78° C. and the reaction mixture was stirred at room temperature for half an hour. The solution was then cooled down to 0° C. and 1.55 g of oxacycloheptadecan-2-one (5.895 mmol; 1 eq.; MW=254.42), dissolved in 5 mL of distilled $CH_2Cl_2$, were added drop by drop. The reaction mixture was left at room temperature under stirring. Thin layer chromatographical analysis showed that the reaction was completed after one hour and a half. The solution was added dropwise into a mixture of 60 mL of $Et_2O/MeOH$ 2:1 cooled to −78° C. and then filtered over celite. 100 mL of a saturated, aqueous solution of $NaHCO_3$ were added and the aqueous phase was extracted with ether. The organic phases were combined, dried over magnesium sulfate and then evaporated under reduced pressure to afford 1.66 g of N-methoxy-N-methyl-16-hydroxyhexadecanamide, corresponding to 5.262 mmol and a yield of 89%. The amide obtained in this way was subsequently used without any additional purification.

$R_f$=0.1; eluant: 30% ethyl acetate in hexane

NMR $^1$H (300 MHz, CDCl$_3$) δ: 1.24 (s broad, 22H, H-4 to H-14); 1.52-1.63 (m, 4H, H-3 and H-15); 2.39 (t, 2H, J=7.7 Hz, H-2); 3.16 (s, 3H, H-1'); 3.61-366 (m, 5H, H-16 and H-2')

NMR $^{13}$C (75 MHz, CDCl$_3$) δ: 24.6 (CH$_2$, C-14); 25.7 (CH$_2$, C-3); 29.4-29.6 (10×CH$_2$, C-4 to C-13); 31.9 (CH$_2$, C-2); 32.0 (CH$_3$, C-1'); 32.8 (CH$_2$, C-15); 61.16 (CH$_3$, C-2'); 63.0 (CH$_2$, C-16)

2. Preparation of N-methoxy-N-methyl-16-benzyloxyhexadecanamide 3.27 g of N-methoxy-N-methyl-16-hydroxyhexadecanamide (10.364 mmol; 1 eq.; MW=315.49) were dissolved with stirring in 40 mL of distilled THF. 0.83 g of NaH, 60% in oil, (20.729 mmol; 2 eq.; MW=24) washed in hexane, was added and the solution was heated under reflux (75° C.) for half an hour. 1.48 mL of BnBr (12.437 mmol; 1.2 eq.; MW=171.04) were added and the solution was heated under reflux. Thin layer chromatographical analysis showed that the reaction was completed after 24 hours. 100 mL of a saturated, aqueous solution of NH$_4$Cl were added and the aqueous phase was extracted with ether. The organic phases were combined, dried over magnesium sulfate and evaporated under reduced pressure to afford a yellow residue. The residue was chromatographed on a silica column (5×15 cm, eluant 30% ethyl acetate in hexane). In total, 2.92 g of N-methoxy-N-methyl-16-benzyloxyhexadecanamide were recovered, corresponding to 7.198 mmol and a yield of 69.4%.

$R_f$=0.5; eluant: 30% ethyl acetate in hexane

NMR $^1$H (300 MHz, CDCl$_3$) δ: 1.25 (s broad, 22H, H-4 to H-14); 1.56-1.65 (m, 4H, H-3 and H-15); 2.40 (t, 2H, J=7.6 Hz, H-2); 3.17 (s, 3H, H-1''); 3.46 (m, 2H, J=6.6 Hz H-16); 3.67 (s, 3H, H-2''); 4.50 (s, 2H, H-17); 7.24-7.34 (m, 5H, H-2' to H-6')

NMR $^{13}$C (75 MHz, CDCl$_3$) δ: 24.6 (CH$_2$, C-15); 26.2 (CH$_2$, C-3); 29.3-29.7 (10×CH$_2$, C-4 to C-14); 31.9 (CH$_2$, C-2); 32.1 (CH$_3$, C-1''); 61.2 (CH$_3$, C-2''); 70.5 (CH$_2$, C-16); 72.8 (Ph-CH$_2$, C-17); 127.4 (Ph, C-4'); 127.6 (Ph, C-2' and C-6'); 128.3 (Ph, C-3' and C-5'); 138.7 (Ph, C-1')

3. Preparation of 17-benzyloxyheptadecan-2-one 0.5 g of N-methoxy-N-methyl-16-benzyloxyhexadecanamide (1.232 mmol; 1 eq.; MW=405.62) was dissolved in 8 mL of THF that had been distilled under argon and cooled down to −78° C. 2.46 mL of MeLi, 1.5 M in ether, (3.698 mmol; 3 eq.; MW=21.95) were added drop by drop at −78° C. Thin layer chromatographical analysis showed that the reaction was instantaneous. 100 mL of a saturated, aqueous solution of NH$_4$Cl were added and the aqueous phase was extracted with ether. The organic phases were combined, dried over magnesium sulfate and evaporated under reduced pressure to afford a yellow residue. The residue was chromatographed on a silica column (5×15 cm, eluant 15% ethyl acetate in hexane). In total, 0.34 g of 17-benzyloxyhexadecan-2-one was recovered, corresponding to 0.941 mmol and a yield of 76.3%.

$R_f$=0.6. eluant: 30% ethyl acetate in hexane

NMR $^1$H (300 MHz, CDCl$_3$) δ: 1.26 (s, broad, 22H, H-5 to H-15); 1.55-1.65 (m, 4H, H-4 and H-16); 2.14 (s, 3H, H-1); 2.42 (t, 2H, J=7.5 Hz, H-3); 3.47 (t, 2H, J=6.6 Hz, H-17); 4.51 (s, 2H, H-18); 7.25-7.36 (m, 5H, H-2' to H-6')

NMR $^{13}$C (75 MHz, CDCl$_3$) δ: 23.9 (CH$_2$, C-4); 26.2-29.8 (13×CH$_2$, C-1, C-5 to C-16); 43.8 (CH$_2$, C-3); 70.5 (CH$_2$, C-17); 72.8 (Ph—CH$_2$, C-18); 127.4 (Ph, C-4'); 127.6 (Ph, C-2' and C-6'); 128.3 (Ph, C-3' and C-5'); 138.7 (Ph, C-1'); 209.4 (C═O)

4. Preparation of 18-benzyloxy-3-methyl-octadec-1-en-3-ol 0.33 g de 17-benzyloxyheptadecan-2-one (0.915 mmol; 1 eq.; MW=360.6) was dissolved in 10 mL of distilled THF with stirring and then cooled down to 0° C. 2.75 mL of vinylmagnesium bromide, 1 M in THF, (2.745 mmol; 3 eq.; MW=g/mol) were added drop by drop at 0° C. The reaction mixture was left at room temperature with stirring. Thin layer chromatographical analysis showed that the reaction was completed after 3 hours. 100 mL of a saturated, aqueous solution of NH$_4$Cl were added and the aqueous phase was extracted with ether. The organic phases were combined, dried over magnesium sulfate and evaporated under reduced pressure to afford a yellow residue. The residue was chromatographed on a silica column (4×15 cm, eluant 20% ethyl acetate in hexane). In total, 0.31 g of 18-benzyloxy-3-methyl-octadec-1-en-3-ol was recovered, corresponding to 0.812 mmol and a yield of 88.7%.

R$_f$=0.7; eluant: 30% ethyl acetate in hexane

NMR $^1$H (300 MHz, CDCl$_3$) δ: 1.26 (s 3H, H-3a); 1.27 (s broad, 24H, H-5 to H-16); 1.54-1.64 (m, 4H, H-4 and H-17); 3.47 (t, 2H, J=6.6 Hz, H-18); 4.51 (s, 2H, H-19); 5.04 (dd, 1H, J$_{1a-1b}$=1.2 Hz, J$_{1a-2}$=10.6 Hz, H$_{1a}$); 5.20 (dd, 1H, J$_{1b-1a}$=1.2 Hz, J$_{1b-2}$=17.3 Hz, H$_{1b}$); 5.91 (dd, 1H, J$_{2-1a}$=10.6 Hz, J$_{2-1b}$=17.3 Hz, H$_{1b}$); 7.26-7.35 (m, 5H, H-2' to H-6')

NMR $^{13}$C (75 MHz, CDCl$_3$) δ: 23.9 (CH$_2$. C-5); 26.2 (CH$_2$. C-6); 27.7 (CH$_3$. C-3a); 29.5-30.0 (11×CH$_2$. C-7 to C-17); 42.4 (CH$_2$. C-4); 70.5 (CH$_2$. C-18); 72.8 (Ph—CH$_2$. C-19); 73.3 (C quaternary, C-3); 111.4 (CH$_2$. C-1) 127.4 (Ph. C-4'); 127.6 (Ph. C-2' and C-6'); 128.3 (Ph. C-3' and C-5'); 138.7 (Ph. C-1'); 145.3 (CH. C-2)

5. Preparation of 2-(15-benzyloxypentadecyl)-2,5,7,8-tetramethylchroman-6-ol 0.11 g of trimethylhydroquinone (0.728 mmol; 1 eq.; MW=152.19) was dissolved in 3 mL of ethyl acetate. 0.08 g of ZnCl$_2$ (0.728 mmol; 0.8 eq.; MW=136.29) then 0.01 mL of concentrated HCl (0.145 mmol; 0.2 eq.; MW=36.46) were added. After 5 minutes at room temperature, 0.28 g of 18-benzyloxy-3-methyl-octadec-1-en-3-ol (0.728 mmol; 1 eq.; MW=388.33) dissolved in 4 mL ethyl acetate was added drop by drop. Thin layer chromatographical-analysis showed that the reaction was completed after 48 hours. 100 mL of a saturated, aqueous solution of NaHCO$_3$ were added and the aqueous phase was extracted with ether. The organic phases were combined, dried over magnesium sulfate and evaporated under reduced pressure to afford a red residue. The residue was chromatographed on a silica column (4×15 cm, eluant 15% ethyl acetate in hexane). In total, 0.29 g of 2-(15-benzyloxypentadecyl)-2,5,7,8-tetramethylchroman-6-ol was recovered, corresponding to 0.554 mmol and a yield of 76%.

Rf=0.74; eluant: 30 ethyl acetate in hexane

NMR $^1$H (300 MHz, CDCl$_3$) δ: 1.22 (s. 3H. H-2a); 1.25 (s broad. 24H. H-2' to H-13'); 1.51-1.66 (m. 4H. H-1' and H-14'); 1.70-1.86 (m. 2H. H-3); 2.11 (s. 6H-5a. H-7a); 2.16 (s. 3H. H-8a); 2.6 (t. 2H. J=6.8 Hz. H-4); 3.46 (t. 2H. J=6.6 Hz. H-15'); 4.18 (s. 1H. phenoxy); 4.50 (s. 2H. H-16'); 7.27-7.35 (m. 5H. H-2" to H-6")

NMR $^{13}$C (75 MHz, CDCl$_3$) δ: 11.3 (CH$_3$. C-5a); 11.8 (CH$_2$, C-7a); 12.2 (CH$_3$, C-8a); 20.7 (CH$_2$. C-4); 23.6 (CH$_2$. C-2'); 23.8 (CH$_3$. C-2a) 26.2 (CH$_3$. C-3'); 29.5-30.0 (11×CH$_2$. C-4' to C-14'); 31.5 (CH$_2$. C-3); 39.5 (CH$_2$. C-1'); 70.5 (CH$_2$. C-15'); 72.8 (Ph-CH$_2$. C-16'); 74.5 (C quaternary, C-2); 117.3 (Ph. C-5); 118.4 (Ph, C-6); 121.0 (Ph, C-8); 122.6 (Ph, C-7); 127.6 (Ph. C-2" and C-6"); 128.3 (Ph. C-3" and C-5"); 138.7 (Ph. C-1"); 144.5 (Ph. C-4a); 145.6 (Ph, C-8b)

6. Preparation of 2-(15-hydroxypentadecyl)-2,5,7,8-tetramethylchroman-6-ol 0.16 g of 2-(15-hydroxypentadecyl)-2,5,7,8-tetramethyl-chromane-6-ol (0.312 mmol; 1 eq.; MW=522.52) was dissolved in 8 mL ethanol. 0.3 g Pd/C (5%) (20% by weight) was added under argon and the argon was then replaced by hydrogen. In all, 3 cycles of vacuum-H$_2$ were made. Thin layer chromatographical analysis showed that the hydrogenation was completed after 4 hours. The solution was filtered through celite and evaporated under reduced pressure to afford a white residue. The residue was chromatographed on a silica column (3×15 cm, eluant 40% ethyl acetate in hexane). In total, 0.13 g of 2-(15-hydroxypentadecyl)-2,5,7,8-tetramethylchroman-6-ol was recovered, corresponding to 0.3 mmol and a yield of 96.4%.

R$_f$=0.56; eluant: 30% ethyl acetate in hexane

NMR $^1$H (300 MHz, CDCl$_3$) δ: 1.22 (s. 3H. H-2a); 1.25 (s broad. 24H. H-2' to H-13'); 1.51-1.61 (m. 4H. H-1 and H-14'); 1.70-1.86 (m. 2H. H-3); 2.11 (s. 6H-5a, H-7a); 2.16 (s. 3H. H-8a); 2.6 (t. 2H. J=6.8 Hz. H-4); 3.64 (t. 2H. J=6.6 Hz. H-15'); 4.24 (s. 1H. phenoxy)

NMR $^{13}$C (75 MHz, CDCl$_3$) δ: 11.3 (CH3. C-5a); 11.8 (CH$_2$, C-7a); 12.2 (CH$_3$, C-8a); 20.7 (CH$_2$. C-4); 23.6 (CH$_2$. C-2'); 23.8 (CH$_3$. C-2a); 26.2 (CH$_3$. C-3'); 29.5-30.0 (11×CH$_2$. C-4' to C-14'); 31.5 (CH$_2$. C-3); 39.5 (CH$_2$. C-1'); 70.5 (CH$_2$. C-15'); 72.8 (Ph-CH$_2$. C-16'); 74.5 (C quaternary, C-2) 117.3 (Ph. C-5); 118.4 (Ph, C-6); 121.0 (Ph, C-8); 122.6 (Ph, C-7); 144.5 (Ph. C-4a); 145.6 (Ph, C-8b)

The compounds in which R$_2$ is equal to a methoxy group or an acetate group (n being equal to 13 et m equal to 1), have been synthesized in the same manner, R$_1$, R$_3$, R$_4$ and R$_5$ being groups as defined in the preceding text, particularly methyl. Other compounds in which R$_1$, R$_3$ or R$_4$ represent a hydroxyl, methoxy or acetate group, the other substituents being as defined in the preceding text, particularly methyl, have also been synthesized.

B. Inhibition of the Activation of the Microglia by TFA (Tocopherol Fatty Alcohols in which R$_1$, R$_3$, R$_4$ and R$_5$ are Methyl Groups and R$_2$ Corresponds to a Hydroxyl Group)

The experiments that were carried out concern the ability of these molecules to inhibit the liberation of nitrites and the Tumor Necrosis Factor-alpha (TNF-α) in the activated microglia. In a further experiment, the expression of MHC II was studied.

1. Measurements of the Release of Nitrites

The activity of the type II NO-synthase (NOS II) represents a parameter for the microglial activation often analyzed in the literature. This enzyme is responsible for synthesizing the nitric oxide radical in inflammatory activation conditions. An activation for 24 to 48 hours produces a large increase in the expression of the enzyme. The product of this enzyme, NO, degrades rapidly in the culture, affording nitrites. Quantitative analysis by colorimetry (Griess method) demonstrates that the levels of $NO_2^-$ follow the same tendency.

In the experiments, the concentrations of $NO_2^-$ in the microglial cell cultures treated with 0.01 µg/ml of LPS, in the presence of the products TFA-10, TFA-12, TFA-14, TFA-16 and vitamin E at concentrations of $10^{-5}$, $10^{-6}$ and $10^{-7}$ M, were measured by the inventors after 24 hours and 48 hours activation. The results obtained from three independent experiments show that the fatty alcohols TFA-10, TFA-12, TFA-14, TFA-16 at concentrations of $10^{-5}$ M bring about a reduction in the production of nitrites by the microglia of up to 50% with respect to the control values. The activity of these products is concentration-dependent as it decreases with the concentration. The products TFA-12, TFA-14, TFA-16 appear to have a higher activity than TFA-10 at $10^{-5}$ M. These results demonstrate that the products according to the invention are able to reduce the production of nitrites by microglial cells activated by LPS. The results demonstrate that there is a connection between the chain length of these products and their activities, because the TFA-10 (which has the shortest chain) exhibits the lowest activity of these tocopherolic fatty alcohols.

2. Measurement of the Release of TNF-α

The expression of the TNF-a represents a parameter for microglial activation often analyzed in the literature. Inactivated microglial does not express this cytokine. A 24 hrs activation by LPS leads to a high increase in the level of TNF-α expression detectable by the ELISA test.

In the experiments, the concentrations of TNF-α in the microglial cell cultures, treated with 0.01 µg/ml of LPS in the presence of TFA-10, TFA-12, TFA-14, TFA-16 and vitamin E, at concentrations of $10^{-5}$, $10^{-6}$ and $10^{-7}$ M, were measured by the inventors after 24 hours activation.

The results obtained from each of the independent experiments concerning TNF-α demonstrate that the tocopherolic fatty alcohols TFA-12, TFA-14 and TFA-16 at $10^{-5}$ M lead to a decrease in production of TNF-α in the cells by 30 to 40% with respect to the controls. The activity of these products is concentration-dependent as it decreases with the concentration. Like vitamin E, the product TFA-10 shows no activity.

These preliminary results on the production of TNF-α confirm the results obtained with the experiments relating to the production of nitrites.

Accordingly, these results demonstrate a connection between the chain length and the activities of the tocopherolic fatty alcohols.

The invention claimed is:

1. A compound of the general Formula (I):

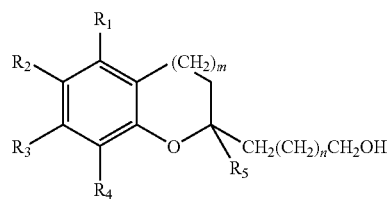

(I)

wherein $R_1$, $R_2$, $R_3$ and $R_4$, identical or different, represent a hydrogen atom, a hydroxyl group, a linear or branched ($C_1$-$C_6$) alkyl group, a linear or branched ($C_1$-$C_6$) alkoxy group, a linear or branched ($C_1$-$C_6$) carboxylate group, $R_5$ represents a hydrogen atom or a linear or branched ($C_1$-$C_6$) alkyl group, m is an integer between 1 and 2, and n is an integer between 8 and 20.

2. The compound according to claim 1, wherein n is an integer between 8 and 16.

3. The compound according to claim 2, wherein n is an integer equal to 8, 10, 12, 13, 14 or 16.

4. The compound according to claim 1, wherein the compound is a compound selected from TFA12, TFA14, TFA15, TFA16 and TFA18.

5. The compound according to claim 1, wherein $R_5$ represents a hydrogen atom or a methyl group.

6. The compound according to claim 1, wherein the carbon atom bearing the substituent $R_5$ has the R or S configuration or is a mixture.

7. The compound of Formula (I) according to claim 1, wherein at least one, of the substituents $R_1$, $R_2$, $R_3$ and $R_4$ on the aromatic ring, represents a hydroxyl, alkoxy or carboxylate group.

8. The compound of Formula (I) according to claim 1, wherein the linear or branched $C_1$-$C_6$ alkyl group is the methyl, ethyl, isopropyl or tert-butyl radical.

9. The compound of Formula (I) according to claim 1, wherein the linear or branched ($C_1$-$C_6$) alkoxy group is the methoxy, ethoxy, isopropoxy or tertiary-butoxy group.

10. A pharmaceutical composition comprising a compound of the general Formula (I):

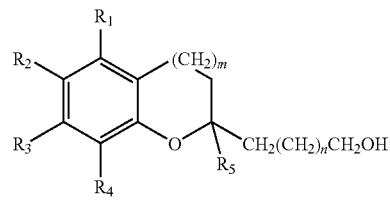

wherein $R_1$, $R_2$, $R_3$ and $R_4$, identical or different, represent a hydrogen atom, a hydroxyl group, a linear or branched ($C_1$-$C_6$) alkyl group, a linear or branched ($C_1$-$C_6$) alkoxy group, a linear or branched ($C_1$-$C_6$) carboxylate group, $R_5$ represents a hydrogen atom or a linear or branched ($C_1$-$C_6$) alkyl group, m is an integer between 1 and 2, and n is an integer between 8 and 20, with a pharmaceutically acceptable carrier.

11. A pharmaceutical composition comprising at least one compound having the following general Formula (I) as the active principle:

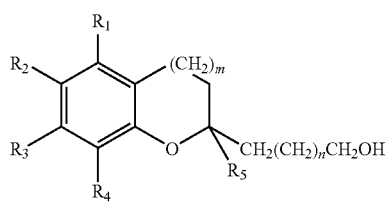

(I)

wherein $R_1$, $R_2$, $R_3$ and $R_4$, identical or different, represent a hydrogen atom, a hydroxyl group, a linear or branched ($C_1$-$C_6$) alkyl group, a linear or branched ($C_1$-$C_6$) alkoxy group, a linear or branched ($C_1$-$C_6$) carboxylate group, $R_5$ represents a hydrogen atom or a linear or branched ($C_1$-$C_6$) alkyl group, m is an integer between 1 and 2, and n is an integer between 8 and 20, for stimulating the modulation of the specification of the neural stem cells and/or the differentiation of cells that are precursors of oligodendrocytes in oligodendroglial cells and/or repressing the activation of microglial cells and/or the activation of astrocytes and/or reactive gliosis, in association with a pharmaceutically acceptable carrier.

* * * * *